United States Patent [19]

Li et al.

[11] Patent Number: 4,624,944
[45] Date of Patent: Nov. 25, 1986

[54] HUMAN SEMINAL ALPHA-INHIBINS

[75] Inventors: Choh H. Li, Berkeley; David Chung, Castro Valley; R. Glenn Hammonds, Jr.; Kristipati Ramasharma, both of San Francisco, all of Calif.

[73] Assignee: The Regents of The University of California, Berkeley, Calif.

[21] Appl. No.: 745,279

[22] Filed: Jun. 14, 1985

[51] Int. Cl.$^4$ .................... A61K 37/43; C07K 7/10
[52] U.S. Cl. ..................................... 514/12; 530/324
[58] Field of Search ................... 260/112.5 R; 514/12; 530/324

[56] References Cited

PUBLICATIONS

Lilja, H., et al., FEBS Lett. 182: 181–184 (1985).
Ramasharma, K., et al., Science 223: 1199–1202 (1984).
Seidah, et al., FEBS Lett. 175: 349–355 (1984).
Sheth, et al., FEBS Lett. 165: 11–15 (1984).
Yamashiro, et al., Proc. Nat'l. Acad. Sci. USA 81: 5399–5402.

Primary Examiner—Delbert R. Phillips
Attorney, Agent, or Firm—Fitch, Even, Tabin & Flannery

[57] ABSTRACT

The present invention discloses novel gonadal peptides with inhibin-like activity. The novel peptides include two gonadal peptides, one consisting of 52 amino acids, the other consisting of 92 amino acids. Both of these peptides were initially isolated from human seminal plasma. Both have now been chemically synthesized. The novel peptides are designated as alpha-inhibin-52 and alpha-inhibin-92. Sequence analyses show that the $NH_2$-terminal 31 amino acids of alpha-inhibin-52 are identical to the structure of the 31 amino acid inhibin-like peptide previously reported by Ramasharma, et al. (1984). Sequence analyses also show that the COOH-terminal 52 amino acids of alpha-inhibin-92 are identical to the structure of alpha-inhibin-52. The amino acid sequence of alpha-inhibin-92 is:

$$\begin{aligned}
& \phantom{\text{H-Thr-Tyr-His-Val-Asp-Ala}}5\\
&\text{H—Thr—Tyr—His—Val—Asp—Ala—Asn—Asp—}\\
& \phantom{\text{-His-Asp-Gln-Ser-Arg}}10\phantom{\text{-Lys-Ser-Gln}}15\\
&\text{—His—Asp—Gln—Ser—Arg—Lys—Ser—Gln—Gln—Tyr—}\\
& \phantom{\text{-Asp-Leu-Asn-Ala-Leu}}20\phantom{\text{-His-Lys-Thr}}25\\
&\text{—Asp—Leu—Asn—Ala—Leu—His—Lys—Thr—Thr—Lys—}\\
& \phantom{\text{-Ser-Gln-Arg-His}}30\phantom{\text{-Leu-Gly-Gly-Ser}}35\\
&\text{—Ser—Gln—Arg—His—Leu—Gly—Gly—Ser—Gln—}\\
& \phantom{\text{-Gln-Leu-Leu-His-Asn}}40\phantom{\text{-Lys-Gln-Glu}}45\\
&\text{—Gln—Leu—Leu—His—Asn—Lys—Gln—Glu—Gly—Arg—}\\
& \phantom{\text{-Asp-His-Asp-Lys-Ser}}50\phantom{\text{-Lys-Gly-His}}55\\
&\text{—Asp—His—Asp—Lys—Ser—Lys—Gly—His—Phe—His—}\\
& \phantom{\text{-Arg-Val-Val-Ile-His}}60\phantom{\text{-His-Lys-Gly}}65\\
&\text{—Arg—Val—Val—Ile—His—His—Lys—Gly—Gly—Lys—}\\
& \phantom{\text{-Ala-His-Arg-Gly-Thr}}70\phantom{\text{-Gln-Asn-Pro}}75\\
&\text{—Ala—His—Arg—Gly—Thr—Gln—Asn—Pro—Ser—Gln—}\\
& \phantom{\text{-Asp-Gln-Gly-Asn-Ser}}80\phantom{\text{-Pro-Ser-Gly}}85\\
&\text{—Asp—Gln—Gly—Asn—Ser—Pro—Ser—Gly—Lys—}\\
& \phantom{\text{-Gly-Ile-Ser-Ser-Gln-Tyr}}92\\
&\text{—Gly—Ile—Ser—Ser—Gln—Tyr—OH}.
\end{aligned}$$

7 Claims, 6 Drawing Figures

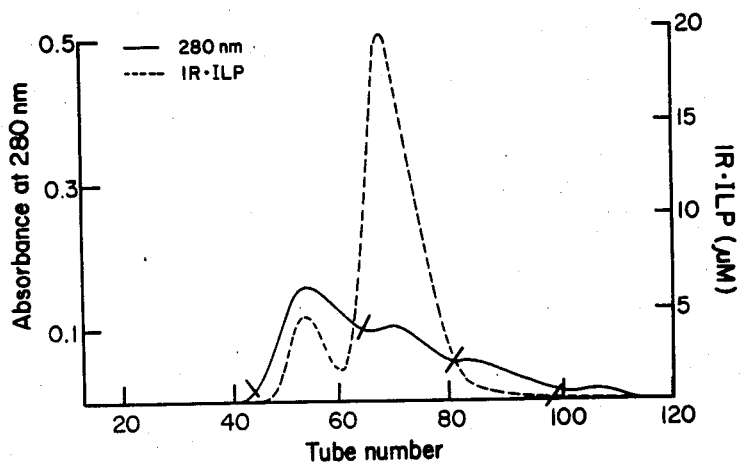
FIG. 1
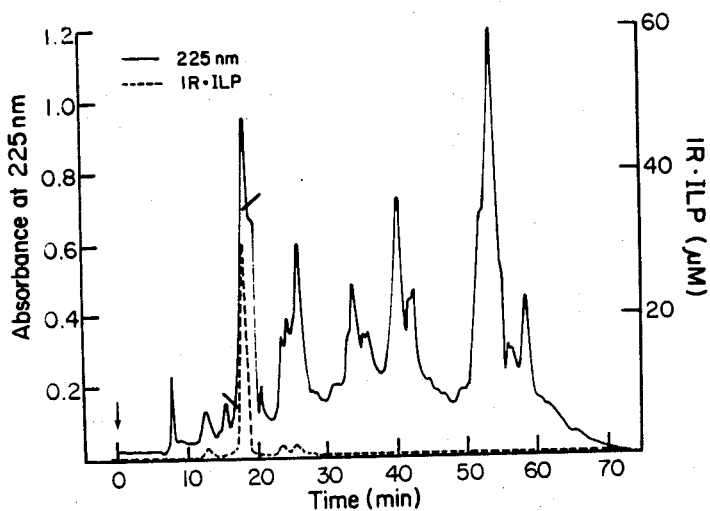
FIG. 2
FIG. 3
```
         1               5                    10
    H-His-Asn-Lys-Gln-Glu-Gly-Arg-Asp-His-Asp-
                        15                   20
      Lys-Ser-Lys-Gly-His-Phe-His-Arg-Val-Val-
               25                    30
      Ile-His-His-Lys-Gly-Gly-Lys-Ala-His-Arg-
                        35                   40
      Gly-Thr-Gln-Asn-Pro-Ser-Gln-Asp-Gln-Gly-
      ←——←——←——←—14→ →——→——→——→——→——→
                              45
      Asn-Ser-Pro-Ser-Gly-Lys-Gly-Ile-Ser-Ser-
      →——→——→——→——→——→←——←—25→ →
       52
      Gln-Tyr-OH
      →——→
```

HUMAN SEMINAL ALPHA-INHIBINS

ACKNOWLEDGMENT

This invention was made with government support under grants from the National Institutes of Health (grants AM-6097 and GM-2907). The U.S. government has certain rights in this invention.

FIELD OF THE INVENTION

This invention relates generally to gonadal peptides. More specifically, this invention relates to novel gonadal peptides that have inhibin-like activity. The novel gonadal peptides of the present invention include human seminal alpha-inhibin-52 and human seminal alpha-inhibin-92, and biologically active fragments thereof.

BACKGROUND OF THE INVENTION

Follicle stimulating hormone (FSH) is one of two pituitary hormones that affect the testes and ovaries. The other is luteinizing hormone (LH). Together FSH and LH stimulate the production of estrogen and progesterone in women, and testosterone in men.

In men, FSH stimulates the production of sperm. Conversely, suppression of FSH production in men leads to a reduction in the production of sperm. As a result, substances that suppress FSH production in men have great potential as male fertility regulating agents. Unfortunately, many of the male fertility regulating agents currently being tested affect both FSH and LH simultaneously, thus sometimes producing undesired impotency as well as the desired infertility.

Inhibins are gonadal peptides that inhibit the release of FSH from the anterior pituitary. The existence of such inhibins was theorized more than 50 years ago when their role was thought to be feedback messengers from the gonads to the pituitary. In this regard it was postulated that the inhibins signal the pituitary gland that it has produced enough follicle stimulating hormone (FSH). The pituitary responds to this information by shutting down production of FSH. See generally, Franchimont, et al. (1979).

Since the inhibins suppress the hormone that stimulates production of sperm, inhibins are likely to inhibit sperm production as well. In addition, the inhibins are likely to suppress sperm production without affecting the production of LH, which is responsible for maintaining sexual libido.

Although the existence of inhibins was postulated more than 50 years ago, isolation and characterization of these putative peptides is just now occurring. For example, the isolation and synthesis of an inhibin-like gonadal peptide (from human seminal plasma) having 31 amino acid residues was recently reported. See Ramasharma, et al. (1984) and Yamashiro, et al. (1984). We have now isolated two additional inhibin-like peptides with activity in suppressing FSH release in vitro. The primary structures of these two new peptides contain the amino acid sequence of the previously reported inhibin-like peptide (ILP).

The previously reported inhibin-like peptide, ILP, was the first human peptide to be isolated and sequenced that had inhibin activity. As a result we refer to ILP and ILP-related inhibins as "alpha" inhibins. Since ILP has 31 amino acids, it is being referred to herein as alpha-inhibin-31 (alpha-IB-31). Since our two new peptides are related to alpha-inhibin-31, and contain 52 and 92 amino acids, respectively, they are referred to herein as alpha-inhibin-52 (alpha-IB-52) and alpha-inhibin-92 (alpha-IB-92).

The amino acid structure of alpha-inhibin-52 was recently reported by Lilja and Jeppson (1985). In addition Sheth, et al. (1984) and Seidah, et al., (1984) recently reported isolation and the complete amino acid sequence of human seminal plasma beta-inhibin. This "beta" peptide consists of 94 amino acids with serine and isoleucine as $NH_2$—and COOH-terminal residues respectively. Beta-inhibin has 5 cystine and 2 tryptophan residues. As will be seen from the disclosure that follows, none of the novel inhibins of the present invention have any cystine or tryptophan residues. Thus it is obvious that the novel inhibins of the present invention are different from beta-inhibin. It is possible these various inhibin-like peptides are derived from a larger inhibin-like protein or inactive precursor molecule.

OBJECTS OF THE INVENTION

It is an object of the present invention to provide novel peptide compositions.

It is a further object of the present invention to provide novel gonadal peptide compositions.

It is a still further object of the present invention to provide novel gonadal peptide compositions that have inhibin-like activity.

Other objects of the invention will become apparent to those skilled in the art from the following description and drawings.

REFERENCE LIST

The present specification refers to the following publications, each of which is expressly incorporated by reference herein.

PUBLICATIONS

1. Barany, G. and Merrifield, R. B., in *The Peptides*, (Gross, E. and Meienhofer, J., eds.), Vol. 2, pp. 1–284, Academic Press, New York (1979).
2. Bhown, A. S., Mole, J. E., Weissinger, A. and Bennett, J. C., *J. Chromatogr.* 148:532–535 (1978).
3. Caruthers, M. H., in *Methods of DNA and RNA Sequencing*, (Weissman, S. M., ed.), pp. 1–22, Praeger Publishers, New York (1983).
4. Franchimont, P., Proyard, J. V., Hagelstein, M. T. H., Renard, C., Demoulin, A., Bourguignon, P. and Hustin, J., *Vitam. Horm.* 37:243–302 (1979). Gait, J. J., (ed.), *Oligonucleotide Syntheses: A Practical Approach*, pp. 1–217, IRL Press, Oxford (1984).
6. Gray, W. R., *Methods in Enzymology*, (Hirs, C. H. W., ed.), Vol. 11, pp. 469–475, Academic Press, New York (1967).
7. Itakura, K., Rossi, J. and Wallace, R., *Ann. Rev. Biochem.*, 53:323–356 (1984).
8. Kulbe, K. D., *Anal. Biochem.* 59:564–573 (1974).
9. Laemmli, U. K., *Nature* 227:680–685 (1970).
10. Lilja, H. and Jeppson, J.-O., *FEBS Lett.* 182:181–184 (1985).
11. Maniatis, T., Fritsch, E. F., and Sambrook, J., *Molecular Cloning, A Laboratory Manual*, Cold Spring Harbor Laboratory, Cold Spring Harbor, N.Y., (1982).
12. Pisano, J. J. and Bronzert, T. J., *Anal. Biochem.* 45:43–59 (1972).
13. Ramasharma, K., Sairam, M. R. and Ranganathan, M. R., *Acta Endocrin.* 98:496–505 (1981).

14. Ramasharma, K., Sairam, M. R., Seidah, N. G., Chretien, M., Manjunath, P., Schiller, P.W., Yamashiro, D. and Li, C. H., *Science* 223:1199–1202 (1984).
15. Reisfield, R. A., Lewis, U. J. and Williams, D. E., *Nature* 195:281–283 (1962).
16. Seidah, N. G., Arbatti, N. J., Rochemont, J., Sheth, A. R. and Chretien, M., *FEBS Lett.* 175:349–355 (1984).
17. Sheth, A. R., Arbatti, N. J., Carlquist, M. and Jornvall, H., *FEBS Lett.* 165:11–15 (1984).
18. Spackman, D. H., Stein, W. H. and Moore, S., *Anal. Chem.* 30:1190–1206 (1958).
19. Yamashiro, D., Li, C. H., Ramasharma, K. and Sairam, M. R., *Proc. Natl. Acad. Sci. USA* 81:5399–5402 (1984).

DRAWINGS

The drawings comprise six FIGURES, of which:

FIG. 1 is a graphical illustration of the fractionation of the precipitate from hSP (3.5 ml) on Sephadex G-50 (fine) column in 0.01 M NH₄OAc (pH 4.6). Flow rate was 30 ml/hr; 3-ml fractions were collected per tube; and void volume was 145 ml. (alpha-IB-31 was formerly designated ILP).

FIG. 2 is a graphical illustration of purification of EC-II (2 mg) on an RP-HPLC column with a linear 2-propanol gradient from 10% to 20% in 0.1% CF₃COOH in 60 min. and a flow rate of 0.5 ml/min.

FIG. 3 is a diagram showing the amino acid sequence of alpha-IB-52. Residues 1-31 constitute alpha-IB-31.

Figure 6:
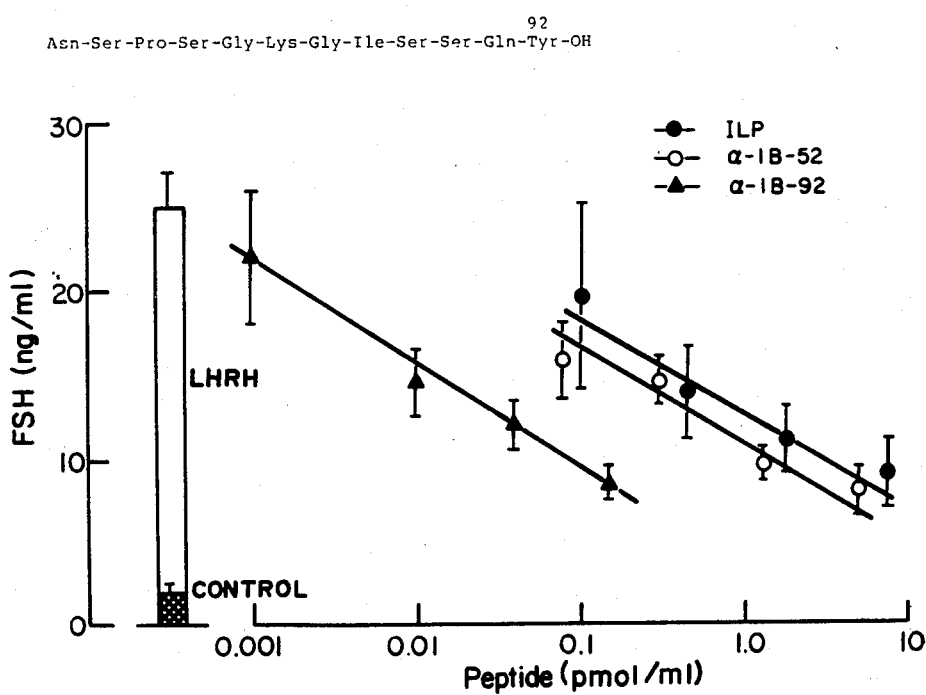

FIG. 6 is a graphical illustration of the effect of alpha-IB-31, alpha-IB-52, and alpha-IB-92 on LHRH-induced FSH secretion by mouse pituitary. Means ±SEM (n=5) are shown. On the graph solid circles represent alpha-IB-31; open circles represent alpha-IB-52; solid triangles represent alpha-IB-92.

DEFINITIONS

In the present specification and claims, reference will be made to phrases and terms of art which are expressly defined for use herein as follows:

As used herein, "alpha-IB-31" means alpha-inhibin-31. "Alpha-IB-31" and "ILP" are synonymous terms.

As used herein, "alpha-IB-52" means alpha-inhibin-52.

As used herein, "alpha-IB-92" means alpha-inhibin-92.

As used herein, "LH" means luteinizing hormone. Luteinizing hormone is also referred to as lutropin. In the present specification and claims "LH" and "lutropin" are used interchangeably.

As used herein, "ILP" means inhibin-like peptide. "ILP" and "alpha-IB-31" are synonymous terms.

As used herein, "IB" means inhibin.

As used herein, "RIA" means radioimmunoassay.

As used herein, "TLC" means thin layer chromatography.

As used herein, "GLC" means gas-liquid chromatography.

As used herein, "HPLC" means high performance liquid chromatography.

As used herein, "RP-HPLC" means reverse-phase high performance liquid chromatography.

As used herein, "TFA" means trifluoroacetic acid.

As used herein, "hSP" means human seminal plasma.

As used herein, "IR" means immunoreactive.

As used herein, "IR-ILP" means immunoreactive inhibin-like peptide.

As used herein, "FSH" means follicle stimulating hormone. Follicle stimulating hormone is also referred to as "follitropin". In the present specification and claims, "FSH" and "follitropin" are used interchangeably.

As used herein, "LHRH" means lutropin (or luteinizing) hormone-releasing hormone.

As used herein, the following amino acids are referred to by the following standard three-letter symbols:

| Amino Acid | Three-Letter Symbol |
|---|---|
| Alanine | Ala |
| Arginine | Arg |
| Asparagine | Asn |
| Aspartic Acid | Asp |
| Cysteine | Cys (half) |
| Glutamine | Gln |
| Glutamic Acid | Glu |
| Glycine | Gly |
| Histadine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

BRIEF DESCRIPTION OF THE INVENTION

The present invention discloses novel gonadal peptides with inhibin-like activity. The novel peptides include two gonadal peptides, one consisting of 52 amino acids, the other consisting of 92 amino acids. Both of these peptides were initially isolated from human seminal plasma. Both have now been chemically synthesized. The novel inhibin peptides are designated as alpha-inhibin-52 and alpha-inhibin-92. Sequence analyses show that the NH₂-terminal 31 amino acids of alpha-inhibin-52 are identical to the structure of the 31 amino acid inhibin-like peptide previously reported by Ramasharma, et al. (1984). Sequence analyses also show that the COOH-terminal 52 amino acids of alpha-inhibin-92 are identical to the structure of alpha-inhibin-52. The amino acid sequence of alpha-inhibin-92 is:

$$\begin{array}{c}5\\\text{H—Thr—Tyr—His—Val—Asp—Ala—Asn—Asp—}\end{array}$$

$$\begin{array}{cc}10 & 15\\\text{—His—Asp—Gln—Ser—Arg—Lys—Ser—Gln—Gln—Tyr—}\end{array}$$

$$\begin{array}{cc}20 & 25\\\text{—Asp—Leu—Asn—Ala—Leu—His—Lys—Thr—Thr—Lys—}\end{array}$$

$$\begin{array}{cc}30 & 35\\\text{—Ser—Gln—Arg—His—Leu—Gly—Gly—Ser—Gln—}\end{array}$$

$$\begin{array}{cc}40 & 45\\\text{—Gln—Leu—Leu—His—Asn—Lys—Gln—Glu—Gly—Arg—}\end{array}$$

$$\begin{array}{cc}50 & 55\\\text{—Asp—His—Asp—Lys—Ser—Lys—Gly—His—Phe—His—}\end{array}$$

-continued

```
            60                      65
—Arg—Val—Val—Ile—His—His—Lys—Gly—Gly—Lys—

70                      75
—Ala—His—Arg—Gly—Thr—Gln—Asn—Pro—Ser—Gln—

80                      85
—Asp—Gln—Gly—Asn—Ser—Pro—Ser—Gly—Lys—

92
                    —Gly—Ile—Ser—Ser—Gln—Tyr—OH.
```

DETAILED DESCRIPTION OF THE INVENTION

The present invention discloses novel and useful inhibin peptides. In preferred forms the novel peptides include alpha-inhibin-92 and alpha-inhibin-52. The entire amino acid sequence of alpha-inhibin-92 is given above. (See the "Brief Description" section, supra). The amino acid sequence of alpha-inhibin-52 is as follows:

```
  1                   5
H—His—Asn—Lys—Gln—Glu—Gly—Arg—Asp—His—

10                  15
Asp—Lys—Ser—Lys—Gly—His—Phe—His—Arg—Val—

20                  25
Val—Ile—His—His—Lys—Gly—Gly—Lys—Ala—His—

30                  35
Arg—Gly—Thr—Gln—Asn—Pro—Ser—Gln—Asp—Gln—

40                  45
Gly—Asn—Ser—Pro—Ser—Gly—Lys—Gly—Ile—Ser—

52
                              Ser—Gln—Tyr—OH.
```

In addition to alpha-inhibin-92 and alpha-inhibin-52, the present invention also discloses and claims useful fragments (F) of essentially pure alpha-inhibin-92. Such fragments include any and all "biologically active" fragments composed of less than the 92 amino acids comprising alpha-inhibin-92, other than the 31 amino-acid fragment composed of:

```
  1                   5
H—His—Asn—Lys—Gln—Glu—Gly—Arg—Asp—His—

10                  15
Asp—Lys—Ser—Lys—Gly—His—Phe—His—Arg—Val—

20                  25
Val—Ile—His—His—Lys—Gly—Gly—Lys—Ala—His—

31
                                 Arg—Gly—OH.
```

For use herein "biologically active" fragments (F) mean, and will be, alpha-inhibin-92 fragments having inhibin-like activity sufficient to suppress lutropin-releasing hormone (LHRH)-induced FSH secretion by the anterior pituitary gland, when such (F) fragments are administered to mammals, including man, in amounts effective to achieve such suppression.

The novel alpha-inhibins of the present invention can be isolated from human seminal plasma. Alternatively they can be easily prepared by utilizing peptide synthesis procedures well known in the art. Preferred peptide synthesis procedures useful in preparing the novel alpha-inhibins of the present invention include solid-phase synthesis methods and automated peptide synthesizers. Such methods were used by Yamashiro, et al. (1984) to synthesize alpha-inhibin-31. The procedures disclosed therein can readily be adapted by those skilled in the art to prepare the novel alpha-inhibins of the present invention. See generally Barany and Merrifield (1979).

The amino acid sequences of the novel alpha-inhibins of the present invention are disclosed herein. Knowing these amino acid sequences, those skilled in the art will readily realize that alpha-IB-52, alpha-IB-92, and biologically active fragments (F) thereof, can also be easily prepared using standard genetic engineering and cloning techniques. For example, nucleic acid sequences coding for the amino acids comprising alpha-IB-52, alpha-IB-92, and biologically active fragments (F) thereof, can easily be synthesized using standard synthesizing methods and machines. Such synthetically prepared DNA coding sequences can then be inserted into suitable cloning vectors, which in turn can be used to transform suitable bacterial hosts so they will produce the novel peptides of the present invention. See generally Maniatis, et al., (1982); Caruthers, (1983); Gait, (1984); and Itakura, et al., (1984).

As the Experimental portion of this specification illustrates, the compounds of the present invention suppress lutropin-releasing hormone (LHRH)-induced FSH secretion by the anterior pituitary gland. Yamashiro, et al., (1984) have shown that inhibin-like peptide (ILP), referred to herein as alpha-inhibin-31, suppresses pituitary FSH secretion in vitro and in vivo. (See *Proc. Nat. Acad. Sci.* 81: at 5400–5401 for specific protocols and a discussion of the Yamashiro, et al. bioassays). As detailed in the Experimental section that follows, our bioassay data in mouse pituitaries in vitro shows that alpha-inhibin-52 is 3.4 times and alpha-inhibin-92 over 40 times more active than inhibin-like peptide (alpha-IB-31) in suppressing follitropin-release. (See Table 1, supra for relative dosage data.)

By utilizing the dosage data contained herein, and standard bioassays such as those disclosed in Yamashiro, et.al. (1984), and the references cited therein, without undue experimentation those skilled in the art can readily determine the biological activity of fragments (F) of alpha-inhibin-92 (i.e., the ability of such fragments (F) to suppress lutropin-releasing hormone (LHRH)-induced FSH secretion by the anterior pituitary gland), as well as the doses thereof that are effective in achieving such FSH suppression.

The novel alpha-inhibins of the present invention can be used as contraceptive agents to suppress LHRH-induced FSH secretion by the pituitary by including them in pharmaceutical preparations having direct or delayed liberation of the active alpha-inhibin ingredients. In preferred forms the pharmaceutical preparations will contain the active alpha-inhibins in association with a compatible pharmaceutical carrier material. This carrier material can be an organic or inorganic inert carrier material, (suitable for anal, percutaneous, insufflatious or oral administration), such as water, gelatin, gum arabic, lactose, starch, magnesium stearate, talc, vegetable oils, polyalkyleneglycols, petroleum jelly, etc. The pharmaceutical preparations will preferably be made up in a solid form (e.g., as tablets, dragees, suppositories or capsules). If necessary the pharmaceutical preparations can be sterilized and/or contain adjuvant substances such as preserving, stabilizing, wetting or emulsifying agents, nontoxic salts or substances acting as buffers.

The pharmaceutical preparations can be prepared in a manner known per se by mixing a compound of the invention with nontoxic solid and/or liquid carrier materials which are customary in pharmaceutical preparations and which are suitable for effective administration (e.g., those carrier materials mentioned earlier) and, if desired, transforming the mixture into the desired pharmaceutical dosage form.

Without further elaboration, it is believed that one of ordinary skill in the art can, using the preceding description, utilize the present invention to its fullest extent. The following experimental section serves to further illustrate amino acid compositions and biological activity of the novel alpha-inhibin peptides of the present invention. It is included for illustrative purposes only and therefore should not be construed as being limitative in any way of the appended claims.

Experimental Materials and Methods

Fresh semen was obtained from men undergoing routine fertility examination in the Department of Urology at the University of California Medical School, San Francisco. Sperm and other cells were removed by centrifugation (5 min at $15,600 \times g$). The supernatant (human seminal plasma, hSP) was acidified to 0.1M HCl by the addition of 6M HCl and stored at $-20°$ C. Trypsin (L-1-tosylamido-2-phenylmethyl chloromethyl ketone-treated 30A872) was obtained from Worthington and carboxypeptidase Y was from Pierce.

Radioimmunoassay was performed with rabbit antiserum to alpha-IB-31. Amino acid analyses were performed in an automatic amino acid analyzer (Model 119C, Beckman) as described by Spackman, et al. (1958). The NH$_2$-terminal residue was determined by the dansyl-Edman procedure (Gray, 1967). For COOH-terminal residue analysis, carboxypeptidase Y digests were carried out in 1M pyridine acetate buffer (pH 5.5) for 4 hr at 37° C. with an enzyme-to-substrate ratio of 1:50. Trypsin digestions were performed with an enzyme-to-substrate ratio of 1:50 in 0.05M Tris/0.01 M Mg$^{2+}$, pH 8.5, at 37° C. for 4 hr.

The dansyl-Edman method was used for manual sequence analysis as described (Gray, 1967). Automatic sequence analysis was performed under the direction of A. Smith of the Protein Structure Laboratory, University of California, Davis, using a Beckman 890M spinning-cup sequenator updated with a cold trap and microprocessor-based programmer. A dilute (0.1M) Quadrol program (Beckman no. 050783) was used. Phenylthiohydantoin derivatives of amino acids were analyzed by GLC (Pisano and Bronzert, 1972), TLC (Kulbe, 1974) and reverse-phase HPLC (RP-HPLC) (Bhown, et al., 1978).

Exclusion chromatography was carried out with a Sephadex G-50 (fine) column ($2.3 \times 75$ cm) with 0.01M NH$_4$OAc buffer (pH 4.6). Each fraction was assayed for immunoreactive (IR) alpha-IB-31 by RIA. Those fractions having immunoreactivity were pooled and lyophilized. Further purification was performed by RP-HPLC in a $4.5 \times 250$ mm column (Vydac 218TP104, Western Analytical Products, Temecula, CA) using a dual pump system from Laboratory Data Control (Riviera Beach, FL) with a variable-wavelength UV detector. Absorption was monitored at 210 or 225 nm. The solvents used were 0.1% CF$_3$COOH and 2-propanol.

Disc electrophoresis in polyacrylamide slab gels was performed as described by Reisfield, et al. (1962). The gels were stained with Coomassie Blue (R250). NaDodSO$_4$ gel electrophoresis was carried out as described by Laemmli (1970). The inhibin activity was assayed by the in vitro mouse pituitary system (Yamashiro, et al., 1984; Ramasharma, et al., 1981).

Results and Discussion

Frozen acidified hSP (7 ml) was thawed and 50 ml of cold ethanol added. After centrifugation, the precipitate was dissolved in 10 ml of 50% HOAc and applied to two separate exclusion chromatography experiments on Sephadex G-50. Two immunoreactive fractions with $V_e/V_o$ of 1.0 (designated EC-I) and 1.4 (designated EC-II) appeared (see FIG. 1). After lyophilization, yields of these fractions were 100 mg (EC-I) and 33 mg (EC-II).

Alpha-IB-52.

Two mg of EC-II were submitted to RP-HPLC, and one major IR-ILP peak was observed (see FIG. 2). When the material in this peak was isolated (0.2 mg) by lyophilization, it behaved as a single component in RP-HPLC. NaDodSo$_4$ gel and disc electrophoresis of the isolated material gave a single band. Histidine was found to be the sole NH$_2$-terminal residue, and tyrosine was at the COOH terminus. Amino acid analysis after a 22-hr hydrolysis in constant boiling HCl gave (sequence values in parenthesis): Asp$_{5.9(6)}$Thr$_{1.1(1)}$Ser$_{5.5(6)}$Glu$_{6.3(6)}$Pro$_{2.1(2)}$Gly$_{7.9(8)}$ Ala$_{1.1(1)}$Val$_{1.9(2)}$Ile$_{1.8(2)}$Tyr$_{0.9(1)}$Phe$_{1.0(1)}$His$_{6.8(7)}$ Lys$_{5.9(6)}$Arg$_{2.7(3)}$. Thus, the peptide consists of 52 amino-acid residues and is referred to herein as alpha-IB-52. From 10 ml hSP, the average yield of alpha-IB-52 was 5 mg.

Tryptic digestion of alpha-IB-52 (30 nmol) was performed, and the digest was fractionated by RP-HPLC using a 2-propanol gradient of 7.5–25% in 0.1% CF$_3$COOH over 60 min. Six tryptic peptides were obtained. Two of these tryptic peptides differed from those obtained from the tryptic digest of alpha-IB-31. They were isolated from the fractions eluted at 14 min and 25 min and called T-14 and T-25. Amino acid composition of T-14 was: Asp$_{2.8(3)}$Thr$_{1.0(1)}$Ser$_{2.8(3)}$Glu$_{3.1(3)}$Pro$_{1.9(2)}$Gly$_{3.0(3)}$ Lys$_{0.9(1)}$. That of T-25 was: Ser$_{1.9(2)}$Glu$_{1.2(1)}$Gly$_{1.2(1)}$Ile$_{1.0(1)}$Tyr$_{0.9(1)}$. Dansyl-Edman analysis of T-25 gave the sequences: H-Gly-Ile-Ser-Ser-Gln-Tyr-OH. This was confirmed by automatic sequence analysis. Since T-25 does not contain lysine or arginine and since tyrosine is the COOH-terminal residue of alpha-IB-52, T-25 must be the COOH-terminal peptide. Peptide T-14 was submitted to automatic sequence analysis. Results are shown in FIG. 3. Since the analyses of the isolated tryptic peptides of both alpha-IB-31 and alpha-IB-52 were identical except for the forementioned two peptides, it is evident that the first 31 amino acids of alpha-IB-52 are identical to the structure of alpha-IB-31.

Alpha-IB-92.

Figure 4:
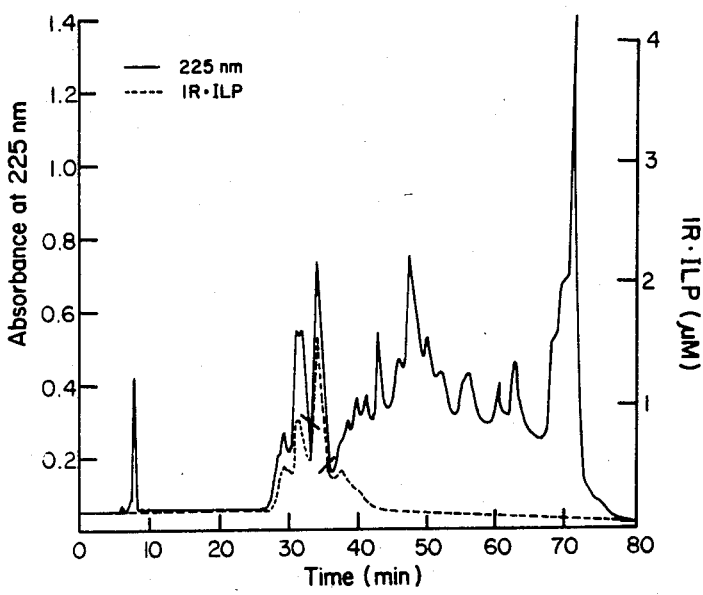
FIG. 4 is a graphical illustration of purification of EC-I (3 mg) on our RP-HPLC column; conditions were the same as for FIG. 2.

Three milligrams of EC-I were chromatographed by RP-HPLC, and several IR-ILP peaks were observed (see FIG. 4). The main IR-ILP peak, eluted at 34 min., was isolated (0.05 mg) and shown to behave as a single component on RP-HPLC, NaDodSO$_4$ gel electrophoresis, and disc electrophoresis. Threonine was the only NH$_2$-terminal residue. Amino acid analyses of alpha-IB-92 gave the following values (sequence values in parenthesis): Asp$_{12.3(12)}$Thr$_{4.1(4)}$Ser$_{9.6(10)}$Glu$_{12.0(12)}$Pro$_{2.5(2)}$Gly$_{10.3(10)}$Ala$_{3.0(3)}$Val$_{3.0(3)}$Ile$_{1.8(2)}$Leu$_{5.0(5)}$ Tyr$_{2.7(3)}$-

$Phe_{1.0(1)}His_{10.4(11)}Lys_{9.2(9)}Arg_{5.2(5)}$. It consists of 92 amino acids and, thus, is designated alpha-IB-92. From 10 ml of hSP, an average yield of 2 mg of alpha-IB-92 may be obtained.

Figure 5:
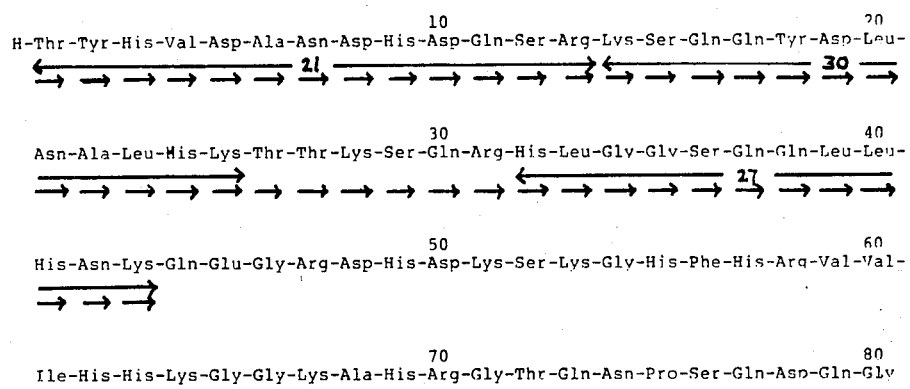
FIG. 5 is a diagram showing the amino acid sequence of alpha-IB-92. Residues 41-92 constitute alpha-IB-52.

A tryptic digest of alpha-IB-92 (30 nmol) was submitted to RP-HPLC as described for alpha-IB-52. Nine tryptic peptides were eluted at 7, 9, 14, 15, 16, 21, 25, 27 and 30 min. Amino acid analyses of these peptides indicated that only three (T-21, T-27, and T-30) are different from those obtained from alpha-IB-52. Their compositions are as follows: T-21, $Asp_{4.3(4)}Thr_{0.9(1)}Ser_{0.8(1)}Glu_{0.9(1)}Ala_{1.0(1)}Val_{1.0(1)}Tyr_{0.7(1)}His_{1.8(2)}Arg_{0.9(1)}$; T-27: $Asp_{1.1(1)}Ser_{0.9(1)}Glu_{2.2(2)}Gly_{2.0(2)}Leu_{3.0(3)}His_{1.8(2)}Lys_{1.0(1)}$; and T-30, $Asp_{2.0(2)}Ser_{1.0(1)}Glu_{2.0(2)}Ala_{0.8(1)}Leu_{2.0(2)}Tyr_{0.6(1)}His_{1.0(1)}Lys_{1.8(2)}$. From these data and the definite occurrence of peptide T-25, it is evident that alpha-IB-52 is located at the COOH-terminus of alpha-IB-92. In order to obtain the primary structure of alpha-IB-92, both T-27 and alpha-IB-92 were submitted to automatic sequence analyses. Results are shown in FIG. 5. Alpha-IB-92 consists of 92 amino acids with three tyrosine residues in positions 2, 18, and 92 and a single phenylalanine residue in position 56. Cystine and tryptophan are absent. The COOH-terminal sequence of residues 41–92 is that of alpha-IB-52. Alpha-IB-92 is a very basic peptide with 5 arginine, 9 lysine, 11 histidine, 1 glutamic acid, and 7 aspartic acid residues. It has unusually high histidine content; more than 10% of the total residues are histidine residues. The $NH_2$-terminal 40-residue segment has only 12 charged groups and is the least hydrophilic part of the molecule.

FIG. 6 presents bioassay data for alpha-IB-31, alpha-IB-52 and alpha-IB-92 in suppressing the lutropin-releasing hormone (LHRH)-induced FSH secretion by using mouse pituitaries in vitro. Alpha-IB-52 is 3.4 times and alpha-IB-92 is 40 times more active than alpha-IB-31 (see Table 1). The addition of 40 amino acids at the $NH_2$-terminus of alpha-IB-52 greatly enhance the inhibin activity.

The immunoreactivity of alpha-IB-52 and alpha-IB-92 is shown in Table 2. Alpha-IB-52 and alpha-IB-92 cross-react to an antiserum raised against alpha-IB-31. They displace labelled $[Tyr^4]$-alpha-IB-31 with 60% of the potency of alpha-IB-31.

TABLE 1

FSH-Suppressing Activity of Alpha-Inhibins

| Peptides | $ED_{50}$ pmol/ml* | Slope | Relative Potency |
|---|---|---|---|
| alpha-IB-31** | 1.02 (0.34–2.9) | 0.548 | 1.0 |
| alpha-IB-52 | 0.30 (0.18–0.52) | 0.414 | 3.4 |
| alpha-IB-92 | 0.025 (0.01–0.049) | 0.487 | 40.5 |

*95% confidence limits are in parenthesis.
**Formerly called ILP

TABLE 2

RIA of Alpha-Inhibins Using Rabbit Antiserum to ILP

| Peptide Ligand | $ED_{50}$ fmoles* | Slope | Relative Potency* |
|---|---|---|---|
| alpha-IB-31** | 38 (29–50) | 1.17 | 1.00 |
| alpha-IB-52 | 65 (45–92) | 0.99 | 0.58 (0.31–1.1) |
| alpha-IB-92 | 63 (42–94) | 1.02 | 0.60 (0.31–1.2) |

*95% confidence limits are in parenthesis.
**Formerly called ILP

SUMMARY

From the foregoing description, one of ordinary skill in the art can easily ascertain that the present invention provides novel gonadal peptides having inhibin activity. These novel peptides include human seminal alpha-inhibin-52, human seminal alpha-inhibin-92, and biologically active fragments thereof. The novel alpha-inhibins of the present invention suppress FSH release without suppressing LH release, and thus are potentially useful as fertility regulating agents.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An essentially pure peptide compound having the formula:

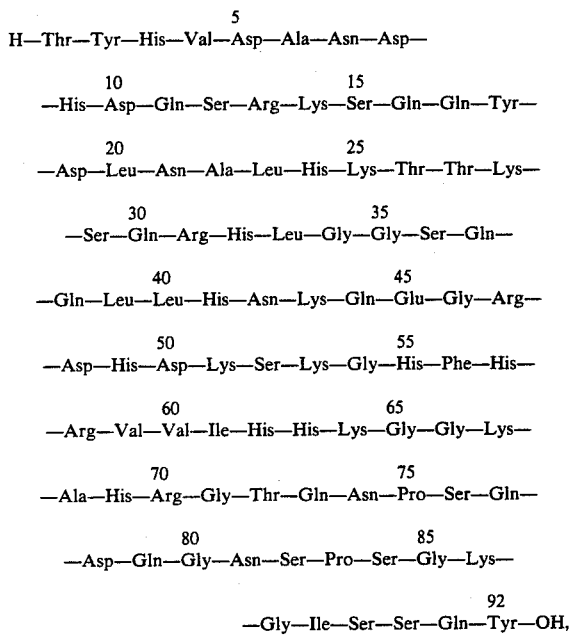

or a nontoxic salt of said peptide.

2. An essentially pure peptide compound having the formula:

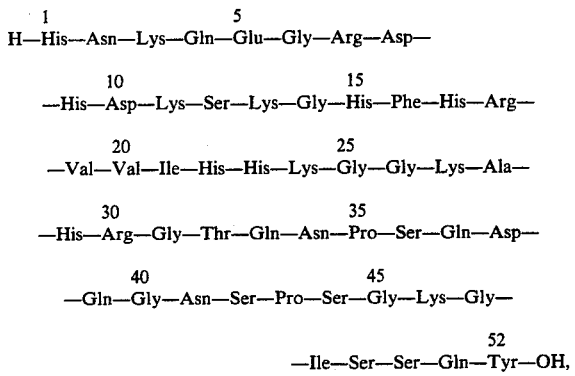

or a nontoxic salt of said peptide.

3. A fragment (F) of the essentially pure alpha-IB-92 peptide compound of claim 1 wherein said fragment (F) is a fragment composed of less than all the 92 amino acids comprising alpha-IB-92; wherein said fragment (F) further is a fragment other than the 31 amino acid fragment alpha-IB-31 composed of:

```
     1                           5
H—His—Asn—Lys—Gln—Glu—Gly—Arg—Asp—His—

10                          15
Asp—Lys—Ser—Lys—Gly—His—Phe—His—Arg—Val—

20                          25
Val—Ile—His—His—Lys—Gly—Gly—Lys—Ala—His—

31
                          Arg—Gly—OH;
``` and wherein said fragment (F) is biologically active in suppressing lutropin-releasing hormone (LHRH)-induced FSH secretion by the anterior pituitary gland; or a nontoxic salt of such peptide fragment (F).

4. A pharmaceutical composition for suppressing lutropin-releasing hormone (LHRH)-induced FSH secretion by the anterior pituitary gland comprising a lutropin-releasing hormone (LHRH)-induced FSH-suppressing amount of essentially pure alpha-IB-92, as disclosed in claim 1, or a fragment (F) thereof, as disclosed in claim 3, or nontoxic salts thereof, in combination with a pharmaceutically acceptable carrier.

5. A pharmaceutical composition for suppressing lutropin-releasing hormone (LHRH)-induced FSH secretion by the anterior pituitary gland comprising a lutropin-releasing hormone (LHRH)-induced FSH-suppressing effective amount of essentially pure alpha-IB-52, as disclosed in claim 2, or a nontoxic salt thereof, in combination with a pharmaceutically acceptable carrier.

6. A method for suppressing FSH secretion by the anterior pituitary gland comprising
administering an effective amount of essentially pure alpha-IB-92, as disclosed in claim 1, or a fragment (F) thereof, as disclosed in claim 3, wherein said effective amount is an amount sufficient to suppress lutropin-releasing hormone (LHRH)-induced FSH secretion by the anterior pituitary gland.

7. A method for suppressing FSH secretion by the anterior pituitary gland comprising
administering an effective amount of essentially pure alpha-IB-52, as disclosed in claim 2, wherein said effective amount is an amount sufficient to suppress lutropin-releasing hormone (LHRH)-induced FSH secretion by the anterior pituitary gland.

* * * * *